US00PP28228P3

(12) United States Plant Patent
Olesen

(10) Patent No.: US PP28,228 P3
(45) Date of Patent: Aug. 1, 2017

(54) COMPACT FLORIBUNDA ROSE PLANT NAMED 'POULPAL063'

(50) Latin Name: ***Rosa* hybrid**
Varietal Denomination: Poulpal063

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/756,267

(22) Filed: Aug. 20, 2015

(65) Prior Publication Data

US 2017/0055397 P1 Feb. 23, 2017

(51) Int. Cl.
*A01H 5/02* (2006.01)

(52) U.S. Cl.
USPC ..... Plt./145

(58) Field of Classification Search
USPC ..... Plt./141, 145
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the compact floribunda class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal063'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulpal063', originated as a single seedling from the stated cross.

The new variety may be distinguished from its male pollen parent and female seed parent primarily by the following characteristics. The female seed parent has flowers which are Yellow Group 10C. while the new variety has flowers which are Yellow Group 10A. The male pollen parent grows to a height of 100 cm while the new variety is more compact, growing to a height of about 50 cm.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal063' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulpal063' was selected in the spring of 2007 by the inventor as a single plant from the progeny of the aforementioned hybridization.

Asexual reproduction of 'Poulpal063' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulpal063' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal063'.

Specifically illustrated in FIG. 1 are open flower, petals detached, bare stems, cluster of flowers on a branch, sepals detached, and reproductive flower parts.

Figure 1:
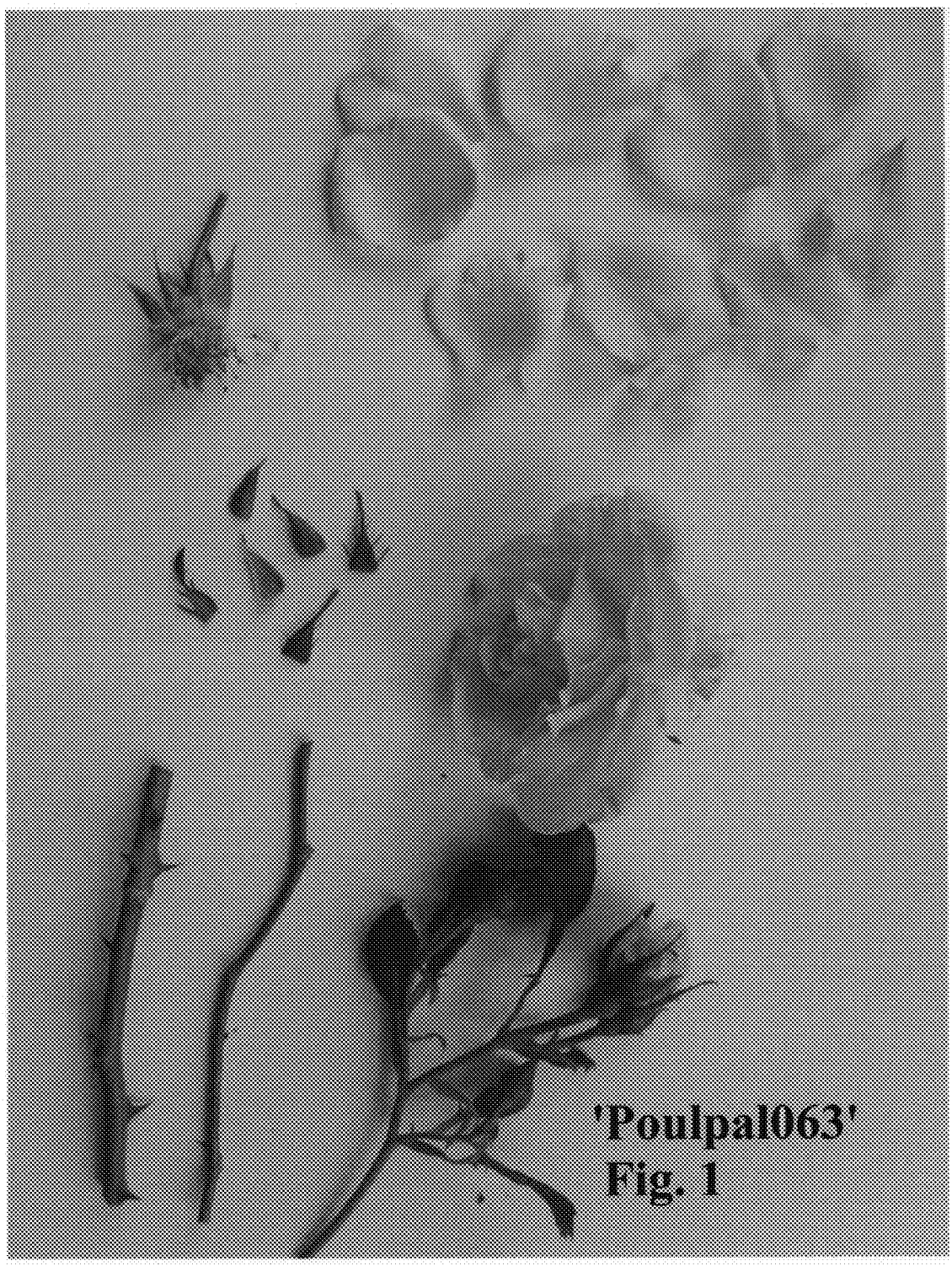
Figure 2:
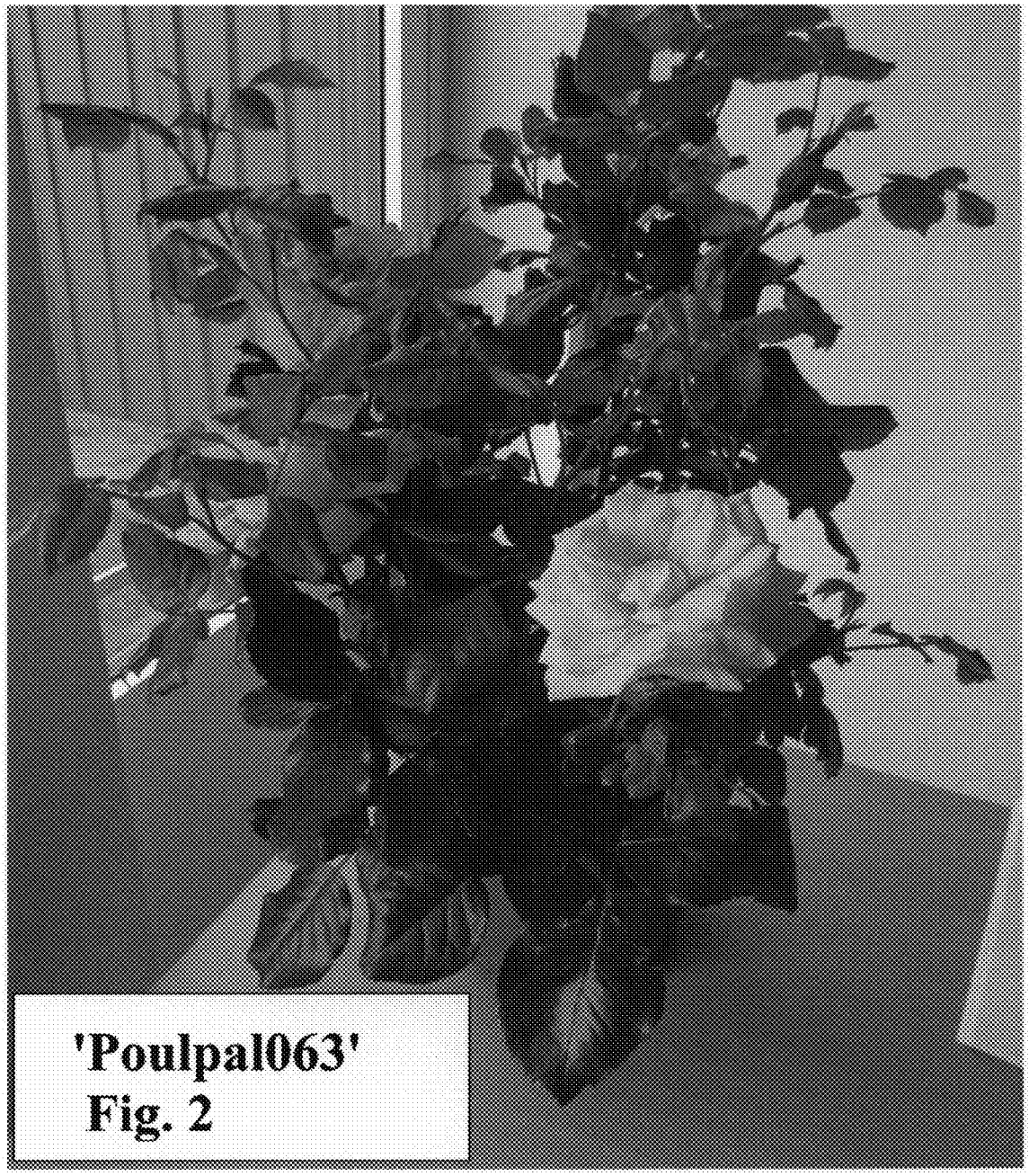

Specifically illustrated in FIG. 2 is the whole plant flowering in a container. Plants shown are 1 year of age.

DETAILED DESCRIPTION OF THE VARIETY

The following is a description of 'Poulpal063', as observed in its growth in Odense Denmark. Observed plants are 1 year old, and were grown on their own roots in 23 cm containers. Color references are made using The Royal Horticultural Society (London, England) Colour Chart, 2001, except where common terms of color are used.

For a comparison, several physical characteristics of the rose variety 'Poulac008', U.S. Plant Pat. No. 15,499 are compared to 'Poulpal063' in Chart 1.

CHART 1

| | 'Poulpal063' | 'Poulac008' |
|---|---|---|
| Petal Count | 45 | 70 to 75 |
| Flower Diameter | 70 to 90 mm | 65 to 70 mm |
| General Tonality of Flower Color | Yellow Group 10A | Yellow Group 12A |

FLOWER AND FLOWER BUD

Blooming habit: Continuous.

Flower bud:

*Size.*—Upon opening, 27 mm in length from base of receptacle to end of bud. Bud diameter is 10 mm.

*Bud form.*—Ovoid.

*Bud color.*—As sepals divide petals are Yellow Group 4A.

*Sepal inner surface.*—Color: Yellow-Green Group 146C. Surface: Lightly pubescent.

*Sepal outer surface.*—Color: Yellow-Green Group 146B with intonations of Greyed-Purple Group 184A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long, 8 mm wide.

*Receptacle.*—Texture: Smooth. Size: 7 mm in height, 8 mm wide. Color: Yellow-Green Group 144A. Shape: Campanulate.

*Pedicel.*—Surface: Smooth. Some pedicels have stipitate glands. Length: About 35 mm. Diameter: 3 mm on average. Color: Yellow-Green Group 144A. Strength: Moderate.

*Peduncle.*—Length: 10 to 25 cm. Diameter: About 4 mm. Color: Yellow-Green Group 144A. Texture: Smooth.

Flower bud development: Flower buds are borne in panicles of up to 12 flower buds per stem. Panicles are about 20 cm in diameter.

Flower bloom:

*Fragrance.*—Moderate spicy scent.

*Duration.*—The blooms have a duration on the plant of approximately 10 days. Petals fall cleanly away from plant after flowers have fully matured.

*Size.*—Flower diameter is 90 mm when open. Flower depth is 35 mm.

*Flower shape.*—Rosette. Very double flower with many slightly overlapping petals of different sizes.

*Shape of flower, side view.*—The upper and lower portions are flat.

Petalage: Under normal conditions, flowers have 45 petals total, 7 of which are petaloids.

General tonality of flower: Open flowers are Yellow Group 10A.

Petal color:

*Upon opening, outer petals.*—Upper surface: Yellow Group 13B. Lower surface: Yellow Group 13B.

*Upon opening, inner petals.*—Upper surface: Yellow Group 13A. Lower surface: Yellow Group 13A. No distinctive coloration at the petal base observed.

*After opening, outer petals.*—Upper surface: Yellow Group 11A. Lower surface: Yellow Group 11A.

*After opening, inner petals.*—Upper surface: Yellow Group 12B. Lower surface: Yellow Group 12B. No distinctive coloration at the petal base observed.

Petals:

*Petal reflex.*—Weak.

*Margin.*—Entire and uniform with an occasional cleft. Undulations not observed.

*Shape.*—Generally broad elliptic. Apex shape: Rounded, or emarginate. Base shape: Rounded.

*Size.*—25 mm (l)×40 mm (w).

*Texture.*—Slightly textured.

*Thickness.*—Average.

Petaloids:

*Size.*—15 mm (l) by Y 10 mm (w).

*Quantity.*—About 7.

*Shape.*—Irregular and asymmetric. The apex and base are acute.

*Color.*—Yellow Group 11A on the upper and lower surface.

Reproductive flower parts:

*Pollen.*—None observed.

*Anthers.*—Size: 2 mm in length. Color: Yellow-Orange Group 22A. Quantity: 100 on average.

*Filaments.*—Color: Yellow Group 13A. Length: 4 to 8 mm.

*Pistils.*—Length: 3 mm. Quantity: About 50.

*Stigmas.*—Color: Yellow Group 4B.

*Styles.*—Color: Red Group 44A.

*Location of stigmas.*—Inferior in location relative to the length of the filaments and the height of the anthers.

*Hips.*—None observed to date.

PLANT

Plant growth: Upright, bushy. Plants are 50 cm in height, and 40 cm wide.

Stems:

*Color.*—Juvenile growth: Yellow-Green Group 144A. Mature growth: Yellow-Green Group 146B.

*Length.*—On average, canes are 45 cm from the base of the plant to the flowering portion.

*Diameter.*—7 mm.

*Internodes.*—On mature canes about 50 mm between nodes.

*Surface texture.*—Young wood: Smooth. Older wood: Smooth.

Long prickles:

*Incidence.*—8 prickles per 10 cm of stem.

*Size.*—Average length of prickles on mature stems is 7 mm.

*Shape.*—Upper portion is concave. Lower portion is deep concave.

*Color.*—Juvenile prickles: Greyed-Red Group 181A. Mature prickles: Greyed-Red Group 182A.

Plant foliage:

*Compound leaf.*—160 mm (l)×120 (w).

*Quantity.*—2 leaves per 10 cm of stem on average.

*Leaf bearing angle to the stem.*—60 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 15 mm long, 8 mm wide. Quantity: 2 per compound leaf. Shape: Linear, slightly broad based with outward extending apices. Margins: Finely serrated. Color: Yellow-Green Group 146A.

*Petiole*.—Length: About 25 mm. Diameter: 2 mm.

*Upper surface*.—Color: Yellow-Green Group 146A.

*Lower surface*.—Color: Yellow-Green Group 144A.

*Rachis*.—Length: 20 mm. Upper surface: Color: Yellow-Green Group 146A.

*Lower surface*.—Color: Yellow-Green Group 144A. Observations: Small prickles.

*Leaflet*.—Quantity: Normally 5 leaflets. Margins: Serrated. Size: On average terminal leaflets are 70 mm long, 55 mm wide. Shape: Generally ovate. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the compact floribunda rose class named 'Poulpal063', substantially as illustrated and described herein, due to its abundant yellow flowers, disease resistance, and extended period of bloom.

* * * * *

'Poulpal063'

'Poulpal063'